(12) United States Patent
Gießen et al.

(10) Patent No.: US 11,406,249 B2
(45) Date of Patent: Aug. 9, 2022

(54) ENDOSCOPE AND IMAGING DEVICE FOR AN ENDOSCOPE

(71) Applicants: Karl Storz SE & Co. KG, Tuttlingen (DE); Universität Stuttgart, Stuttgart (DE)

(72) Inventors: Harald Gießen, Marnheim (DE); Alois Herkommer, Stuttgart (DE); Simon Thiele, Stuttgart (DE); Klaus Irion, Tuttlingen (DE); Werner Göbel, Tuttlingen (DE); Benjamin Häsler, Tuttlingen (DE)

(73) Assignees: KARL STORZ SE & CO. KG, Tuttlingen (DE); UNIVERSITAT STUTTGART, Stuttgart (DE)

( * ) Notice: Subject to any disclaimer, the term of this patent is extended or adjusted under 35 U.S.C. 154(b) by 327 days.

(21) Appl. No.: 16/400,357

(22) Filed: May 1, 2019

(65) Prior Publication Data

US 2019/0350442 A1 Nov. 21, 2019

(51) Int. Cl.
*A61B 1/00* (2006.01)
*G02B 23/24* (2006.01)
(Continued)

(52) U.S. Cl.
CPC ...... *A61B 1/00174* (2013.01); *A61B 1/00188* (2013.01); *G02B 23/243* (2013.01);
(Continued)

(58) Field of Classification Search
CPC ............ A61B 1/00174; A61B 1/00188; A61B 1/00167; A61B 1/00195; A61B 1/0051;
(Continued)

(56) References Cited

U.S. PATENT DOCUMENTS 5,327,283 A * 7/1994 Zobel .................. G02B 23/243
359/717
5,573,493 A * 11/1996 Sauer ................. A61B 1/00096
600/177

(Continued)

FOREIGN PATENT DOCUMENTS

DE         697 34 638 T2    6/2006
DE   10 2011 089 157 A1    6/2013
(Continued)

OTHER PUBLICATIONS

Search Report, EP 19172294.1, dated Oct. 24, 2019 (in German) (14 pp.).
(Continued)

*Primary Examiner* — Timothy J Neal
*Assistant Examiner* — Sung Ham
(74) *Attorney, Agent, or Firm* — Eversheds Sutherland (US) LLP (57) ABSTRACT

An endoscope includes a shaft having a distal end, an optical imaging device at the distal end of the shaft for producing a real image of an object observed by means of the endoscope and at least one of an image transfer device for transmitting the real image and an image sensor for capturing the real image. The imaging device has curved light-refracting interfaces, which are tilted in relation to one another.

13 Claims, 3 Drawing Sheets

(51) Int. Cl.
    *A61B 1/005* (2006.01)
    *A61B 1/04* (2006.01)
(52) U.S. Cl.
    CPC ......... *A61B 1/0051* (2013.01); *A61B 1/00167* (2013.01); *A61B 1/00195* (2013.01); *A61B 1/04* (2013.01)
(58) Field of Classification Search
    CPC ... A61B 1/04; A61B 1/00179; A61B 1/00096; A61B 1/00181; A61B 1/00183; A61B 1/0011; G02B 23/243; G02B 23/2469; G02B 3/02
    USPC .................................................. 600/129, 160
    See application file for complete search history.

(56) References Cited

U.S. PATENT DOCUMENTS

| | | | | |
|---|---|---|---|---|
| 5,912,764 | A * | 6/1999 | Togino | A61B 1/00179 359/367 |
| 6,128,144 | A * | 10/2000 | Togino | G02B 7/10 359/728 |
| 6,327,094 | B1 * | 12/2001 | Aoki | G02B 13/22 359/631 |
| 2003/0179464 | A1 * | 9/2003 | Amanai | G02B 17/0896 359/685 |
| 2005/0250992 | A1 * | 11/2005 | Scherr | A61B 1/07 600/182 |
| 2007/0088203 | A1 * | 4/2007 | Lau | A61B 17/0218 600/205 |
| 2013/0267778 | A1 * | 10/2013 | Rehe | A61B 1/00142 600/125 |
| 2014/0236024 | A1 * | 8/2014 | Bierhoff | A61B 18/1477 600/478 |
| 2017/0336609 | A1 * | 11/2017 | Lerner | G02B 21/22 |
| 2018/0017806 | A1 * | 1/2018 | Wang | G01B 9/02044 |
| 2018/0281324 | A1 * | 10/2018 | Gießen | B29D 11/00951 |
| 2018/0344130 | A1 * | 12/2018 | Gmeiner | A61B 1/00165 |
| 2019/0260927 | A1 * | 8/2019 | Thiele | G03F 7/0015 |

FOREIGN PATENT DOCUMENTS

| | | |
|---|---|---|
| DE | 10 2015 003 652 A1 | 9/2016 |
| DE | 10 2015 103 214 A1 | 9/2016 |
| DE | 102015103214 * | 9/2016 |
| DE | 10 2015 012 980 A1 | 4/2017 |
| EP | 0 647 425 A1 | 4/1995 |
| EP | 0 845 692 A2 | 6/1998 |
| EP | 2 037 307 A1 | 3/2009 |
| EP | 2 056 150 A1 | 5/2009 |
| EP | 3 162 549 A1 | 10/2015 |
| EP | 1 961 371 B1 | 3/2017 |
| WO | 2009019703 A2 | 2/2009 |
| WO | 2009019703 A3 | 2/2009 |
| WO | 2017059960 A1 | 4/2017 |

OTHER PUBLICATIONS

Search Report, DE 10 2018 110 523.1, dated Oct. 8, 2018 (in German) (7 pp.).
Search Report, DE 10 2018 110 523.1, dated Oct. 8, 2018 (in English) (9 pp.).

* cited by examiner

ENDOSCOPE AND IMAGING DEVICE FOR AN ENDOSCOPE

TECHNICAL FIELD

The present invention relates to an endoscope and an imaging device for producing a real image of an object observed by means of the endoscope.

BACKGROUND OF THE INVENTION

An optical inspection of thin-caliber cavities or hollow organs is diagnostically advantageous and desirable in many medical branches of medicine. Examples include dental root canals with a typical diameter of 0.5 mm or less, salivary ducts with a typical diameter of 1 mm or less, Eustachian tubes with a typical diameter of 1.5 mm or less and lactiferous ducts with a typical diameter of 1.3 mm or less. Further, an optical inspection of the inner walls of blood vessels or lymph vessels—in the case of suitable rinsing—may be diagnostically advantageous and desirable in future. An optical inspection of alveoli would be diagnostically advantageous and desirable within the scope of bronchoscopy. An optical inspection of an embryo in the womb, too, would be diagnostically advantageous and desirable. These applications require correspondingly thin optical inspection instruments, in particular endoscopes.

Novel manufacturing methods facilitate ever more precise manufacturing of ever smaller structures, even those made of optical transparent materials.

EP 1 961 371 B1 describes an illumination device for an image capture device at the distal end of an endoscope. Microlenses are provided for beam shaping (paragraph [0024]).

DE 10 2015 003 652 A1 has described a method for connecting a solid core optical fiber with a further optical fiber and a method for providing a solid core optical fiber with a joining device for connecting the solid core optical fiber to a further optical fiber (title, paragraphs [0015], [0016]). The joining device is applied to the axial end of the solid core fiber by means of 3D printing on the basis of two-photon polymerization (paragraphs [0016], [0021]).

DE 10 2015 012 980 A1 has described a method and a device for producing micro-structures on optical fibers by means of a 3D printer (title, paragraphs [0007], [0009], [0058], [0064], [0067]). In the process, use can be made of two-photon polymerization (paragraph [0059]).

EP 3 162 549 A1 has described a method and a device for producing an optical element comprising a stop or a structure for stray-light absorption (title, paragraphs [0004], [0008], [0012]). A three-dimensional structure with a microfluidic cavity is formed by means of a 3D printer and the microfluidic cavity is subsequently filled with a functional substance using the capillary effect (paragraph [0015]).

SUMMARY OF THE INVENTION

It is an object of the present invention to develop an improved endoscope and an improved method for producing an imaging device for an endoscope.

This object is achieved by the subject matter of the independent claims.

Developments are specified in the dependent claims.

An endoscope comprises a shaft comprising a distal end, an optical imaging device at the distal end of the shaft for producing a real image of an object observed by means of the endoscope and at least one of an image transfer device for transmitting the real image and an image sensor for capturing the real image, wherein the imaging device has curved light-refracting interfaces, which are tilted in relation to one another.

The endoscope is provided for medical applications in particular, for example as a sialendoscope for the optical inspection of a salivary duct, as a fetoscope for the optical inspection of an unborn fetus in the amniotic sac, as a cystoscope for cystoscopy, as a root canal endoscope for the optical inspection of the root canal of a tooth in endodontics, or for ductoscopy, i.e., for the optical inspection of a milk duct of a mammary gland. Alternatively, the endoscope can be provided and embodied for technical applications.

The shaft of the endoscope is particularly long and thin. The shaft can be straight or curved, rigid or flexible.

By way of example, the image transfer device may comprise a plurality of rod lenses arranged in succession or any other relay lens system or a coherent bundle of optical fibers. The image transfer device transfers the real image produced by the optical imaging device to a proximal end of the endoscope, in particular. At the proximal end of the endoscope, the transferred real image can be directly observed through an eyepiece or else it can be captured by a camera coupled to the eyepiece or by one or more image sensors that are optically coupled to the endoscope in a different way or that are integrated in the endoscope and can be converted into an image signal. Alternatively, an image sensor or a plurality of image sensors is/are arranged directly on the imaging device in order to capture the real image produced by the imaging device and convert this into an analog or digital image signal.

In particular, the curved light-refracting interfaces are tilted in relation to one another in such a way that there is no common axis of symmetry, in respect of which all curved light-refracting interfaces would be rotationally symmetric. In particular, the surface normals of the curved light-refracting interfaces at the vertices or at the surface center points thereof are not parallel to one another and/or not parallel to a connecting straight line between the vertices or surface center points. Alternatively, the mean surface normals of the curved light-refracting interfaces could be not parallel to one another and/or not parallel to a connecting straight line between the vertices or surface center points of the curved light-refracting interfaces, for example. This arrangement and alignment of the curved light-refracting interfaces is also referred to as off axis. In addition to two or more curved light-refracting interfaces that are tilted in relation to one another, the imaging device may also comprise one or more further curved light-refracting interfaces, which are arranged in parallel or symmetrically with respect to a common optical axis in relation to one another or in relation to one of the curved light-refracting interfaces that are tilted in relation to one another.

An imaging device with curved light-refracting interfaces, which are tilted in relation to one another, facilitates unusual imaging properties, for example a deviation of the viewing direction from the surface normal of the real image produced by the optical imaging device, a distortion or rectification and/or a non-parallelism of object surface and image surface.

The diameter of the shaft of an endoscope as described here is no greater than 3 mm or no greater than 1.5 mm or no greater than 1.0 mm or less than 1.0 mm, in particular.

The diameter of the imaging device of an endoscope as described here is no greater than 3 mm or no greater than 1.5 mm or no greater than 1.0 mm or less than 1.0 mm, in particular.

In an endoscope as described here, one of the curved light-refracting interfaces of the imaging device, in particular, is not rotationally symmetric.

A curved light-refracting interface is not rotationally symmetric if there is no axis of symmetry in respect of which the curved light-refracting interface would be rotationally symmetric. The imaging device may comprise a plurality of curved light-refracting interfaces, each of which is not rotationally symmetric.

In an endoscope as described here, one of the curved light-refracting interfaces of the imaging device, in particular, is not a section of a rotationally symmetric curved surface.

In particular, a plurality or all of the curved light-refracting interfaces of the imaging device are not sections of rotationally symmetric curved surfaces.

In an endoscope as described here, one of the curved light-refractive interfaces, in particular, is a free-form surface.

In particular, a plurality or all of the curved light-refracting interfaces can be free-form surfaces. A free-form surface refers, in particular, to a surface that is not a section of a surface of a sphere or of an ellipsoid of revolution or of a hyperboloid of revolution.

Configuring one or more curved light-refracting interfaces of the imaging device as free surfaces may facilitate comprehensive matching of the optical properties of the imaging device to requirements of the intended application and, at the same time, a high imaging quality.

In an endoscope as described here, the viewing direction of the endoscope is not parallel, in particular, to the longitudinal axis of the distal end of the shaft of the endoscope.

In particular, the viewing direction of the endoscope is the direction in which an object lies, said direction being related to the center of the light-entrance surface of the endoscope and said object being imaged in the center of an image captured by means of the endoscope. Particularly in the case of distorted imaging with significantly different imaging scales at different points of the image, the viewing direction of the endoscope can be considered to be the direction from the center of the light-entrance surface of the endoscope to the surface center point of that area that is imaged in focus by the imaging device and that, in its entirety, is transmitted by the image transfer device or captured by the image sensor.

Endoscopes whose viewing direction is not parallel to the longitudinal axis of the shaft (not parallel to the longitudinal axis of the shaft at its distal end in the case of a bent or bendable shaft) are often referred to as side view endoscopes, too. Curved light-refracting interfaces, which are tilted in relation to one another, may facilitate a viewing direction of the endoscope that deviates from the longitudinal axis of the shaft, without requiring reflecting surfaces (at a prism, for example) or an oblique arrangement of the image sensor in the process.

In an endoscope as described here, the angle between the viewing direction of the endoscope and the longitudinal axis of the distal end of the endoscope is, in particular, no less than 10 degrees or no less than 20 degrees or no less than 30 degrees.

In an endoscope as described here, an angle between the viewing direction of the endoscope and the longitudinal axis of the distal end of the endoscope is, in particular, degrees or 30 degrees or 45 degrees or 60 degrees or 70 degrees or 90 degrees or 120 degrees.

In an endoscope as described here, light contributing to the production of the real image is not reflected, in particular.

In an endoscope as described here, no reflecting surface, in particular, is provided upstream of the real image, produced by the imaging device, in relation to the light flux.

In an endoscope as described here, the imaging device, in particular, has no reflecting surface.

Dispensing with a reflecting surface may reduce the installation space required and may simplify precise manufacturing. In particular, there is no need to manufacture and arrange a prism with surface regions providing total-internal reflection.

In an endoscope as described here, the image angle of the endoscope is, in particular, no less than 60 degrees or no less than 70 degrees or no less than 80 degrees or no less than 90 degrees or no less than 100 degrees.

The image angle of an endoscope is, in particular, the angle measured from the center of the light-entrance surface of the endoscope between opposing straight or substantially straight edge sections of that area that is imaged in focus by the imaging device and the real image of which is transmitted, in its entirety, by the image transfer device or captured, in its entirety, by the image sensor. Alternatively, the image angle of an endoscope is, in particular, the angle measured from the center of the light-entrance surface of the endoscope between opposing edge sections of that area that is imaged in focus by the imaging device and the real image of which is transmitted, in its entirety, by the image transfer device or captured, in its entirety, by the image sensor.

Curved light-refracting interfaces, which are tilted in relation to one another, can facilitate a large image angle and, at the same time, a comparatively good imaging quality, even in the case of a viewing direction that is not parallel to the longitudinal axis of the distal end of the shaft of the endoscope.

In the case of an endoscope as described here, the imaging device comprises at least one of plastic or glass and a mixture of plastic and glass, or it is formed, in part or in full, by plastic or glass or a mixture of plastic and glass.

Glass, in the form of nanoparticles or other small particles, may be embedded in a plastic matrix. Different optical properties, for example counteracting dispersion of the glass of the glass particle and of the plastic, may facilitate a reduction in the chromatic aberration, for example.

An endoscope as described here further comprises, in particular, a stop structure for laterally trimming an optical path, with at least one of being produced at the same time as the imaging device and being embedded in the imaging device applying to the stop structure.

The stop structure is formed, in particular, from a light-absorbing material. The stop structure can be arranged at a light-refracting interface (and consequently laterally delimit the latter), between two light-refracting interfaces or, in relation to the propagation direction of light emanating from an observed object, upstream or downstream of all of the light-refracting interfaces of the imaging device. By way of example, the stop structure can be formed by means of 3D printing or by filling a cavity in a transparent body of the imaging device by capillary action.

In an endoscope as described here, the imaging device is produced, in particular, by means of 3D printing based on multi-photon absorption or multi-photon polymerization.

In an endoscope as described here, the imaging device is produced, in particular, by means of 3D printing, wherein the imaging device is printed directly on a distal light-entrance surface of an image transfer device for transmitting the real image or on a light-entrance surface of an image sensor for capturing the real image.

In an endoscope as described here, the imaging device is produced, in particular, from a plurality of different materials by means of 3D printing.

The imaging device is formed, in particular, from a plurality of different materials with different refractive indices. The imaging device is produced, in particular, from a plurality of different liquid photoreactive or photo-curing precursor materials.

In an endoscope as described here, the imaging device comprises, in particular, an interface embodied as a diffractive optical element or any other diffractive optical element.

In particular, the diffractive optical element can facilitate a chromatic correction by virtue of having a dispersion that counteracts that of the optical transparent material of the imaging device.

In an endoscope as described here, the imaging device comprises, in particular, a plurality of optically transparent bodies with the light-refracting interfaces, said bodies, when used as intended, being penetrated by light that emanates from an observed object and contributes to the production of the real image.

In an endoscope as described here, the imaging device comprises, in particular, a plurality of optically transparent bodies with the light-refracting interfaces, said bodies, when used as intended, being penetrated by light that emanates from an observed object and contributes to the production of the real image, wherein a supporting device mechanically rigidly connects the bodies.

In particular, the plurality of optically transparent bodies are arranged in such a way that light that emanates from an observed object and contributes to the production of the real image successively passes through the transparent bodies.

The support device or support structure comprises one or more support struts, for example. The support device or support structure is connected, in particular, to edge regions of the bodies with the light-refracting interfaces. The support device may comprise a plurality of optionally parallel support struts and/or a mesh or grid of support struts.

In an endoscope as described here, the support devices and the transparent bodies that are penetrated by the light and that have the curved light-refracting interfaces are, in particular, at least one of formed by the same material and produced at the same time.

A simultaneous production of the support device and the bodies that are penetrated by the light and that have the curved light-refracting interfaces may facilitate a precise relative arrangement of the curved light-refracting interfaces and consequently make an adjustment obsolete and significantly reduce the manufacturing costs.

An endoscope as described here further comprises, in particular, a light-steering device at the distal end of the endoscope for steering illumination light emanating from a distal light-exit surface of a light guide or from a light-exit surface of a light source, wherein the light-steering device has a light-refracting interface, which is tilted in relation to the longitudinal axis of the distal end of the light guide or in relation to a surface normal of the light-exit surface of the light source.

The endoscope comprises, in particular, a light guide in the form of one or more optical fibers for transferring illumination light to the distal end of the endoscope. The light-steering device may be directly printed on a light-exit surface of the light guide or of the light source.

The light-steering device may comprise a plurality of light-refracting interfaces, illumination light passing therethrough if used as intended and then illuminating objects within the field of view. The light-refracting interfaces of the light-steering device are arranged, in particular, in such a way that illumination light successively passes through the light-refracting interfaces. The light-refracting interfaces therefore are arranged in succession and not next to one another, in particular in relation to the propagation direction of the illumination light.

A light-refracting interface of the light-steering device is tilted, in particular, in relation to the longitudinal axis of the distal end of the light guide or in relation to the surface normal of the light-exit surface of the light source to the extent that the mean surface normal or the surface normal at the surface center point of the light-refracting interface is not parallel to the longitudinal axis of the distal end of the light guide or to the surface normal of the light-exit surface of the light source.

The tilted arrangement of one or more light-refracting interfaces of the light-steering device may replace or render obsolete curving of the distal end of the light guide or tilting of the light source.

In an endoscope as described here, the light-refracting interface of the light-steering device is not rotationally symmetric, in particular.

In an endoscope as described here, the light-refracting interface of the light-steering device, in particular, is not a section of a rotationally symmetric curved surface.

An endoscope as described here further comprises, in particular, a support frame, which rigidly connects the imaging device and the light-steering device to one another.

In an endoscope as described here, at least one of being mechanically rigidly connected to one another and having the same optically transparent material and having a monolithic embodiment and being produced at the same time applies to the imaging device and the light-steering device.

The simultaneous production (for example within the scope of the same 3D printing process) from the same optically transparent material, in particular, may facilitate precise and nevertheless cost-effective manufacturing.

In an endoscope as described here, the light-steering device has, in particular, a cutout for receiving the distal end of a light guide, wherein the cutout defines the position and orientation of the distal end of the light guide.

In particular, the cutout is open in the proximal direction. The cutout has, in particular, the form of a blind hole, the end of which defines the position of the light-exit surface of the light guide. In particular, the form of the cutout is selected in such a way that the light guide is held in interlocking fashion and with little play in the lateral direction.

A method for producing an imaging device for an endoscope comprises, in particular, a step of producing the imaging device by means of 3D printing.

A method for producing an imaging device for an endoscope comprises, in particular, a step of producing a mold for the imaging device and a step of producing the imaging device by making a cast of the mold, wherein the mold is produced by means of 3D printing.

The methods described here for producing an imaging device are suitable, in particular, for producing an imaging device for an endoscope, as described here, and may be part of a method for producing an endoscope. In particular, the methods described here for producing an imaging device may be embodied with features of the imaging device of an endoscope described here.

BRIEF DESCRIPTION OF THE FIGURES

Exemplary embodiments will be explained in more detail below on the basis of the attached figures. In the figures.

DESCRIPTION OF THE EMBODIMENTS

Figure 1:
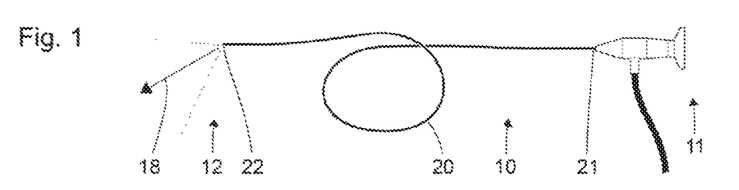
FIG. 1 shows a schematic illustration of an endoscope.

FIG. 1 shows a schematic illustration of an endoscope with a proximal end 11 and a distal end 12. The endoscope 10 has a viewing direction 18, indicated by an arrow in FIG. 1, and a field of view or visual field, the edges of which are indicated by dashed lines.

The endoscope 10 has a long and thin shaft 20 with a proximal end 21 near the proximal end 11 of the endoscope. In the example illustrated in FIG. 1, the cross section of the shaft 20 is constant or substantially constant over the entire length of the shaft 20. Deviating from the illustration in FIG. 1, the cross section of the shaft may vary. A distal end 22 of the shaft 20 forms the distal end 12 of the endoscope 10. In the illustrated example, the viewing direction 18 of the endoscope 10 is not parallel to the longitudinal axis of the shaft 20 in the vicinity of the distal end 22 thereof.

The shaft 20 is flexible in the illustrated example. By way of example, the endoscope 10 is a sialendoscope for the optical inspection of a salivary duct, a fetoscope for the optical inspection of a fetus in the amniotic sac of the mother or a cystoscope for cystoscopy. Alternatively, the endoscope 10 may be provided and embodied, for example, for the optical inspection of the root canal of a tooth in endodontics, or for ductoscopy, i.e., for the optical inspection of a milk duct of a mammary gland.

At its distal end 12, the endoscope 10 comprises an optical imaging device for producing a real image. Further, the endoscope 10 may comprise one or more image sensors at its distal end 12 for capturing the real image produced by the imaging device. Alternatively, the endoscope 10 may comprise an image transfer device for transmitting the real image produced by the imaging device to the proximal end 11 of the endoscope. In this case, the real image transmitted to the proximal end 11 can be observed through an eyepiece, as indicated in FIG. 1, and/or can be captured by means of one or more image sensors which produce an image signal. One or more image sensors may be integrated in the endoscope 10 near the proximal end 11 thereof or may be a constituent part of a camera that is optically and mechanically couplable to the eyepiece of the endoscope.

Figure 2:
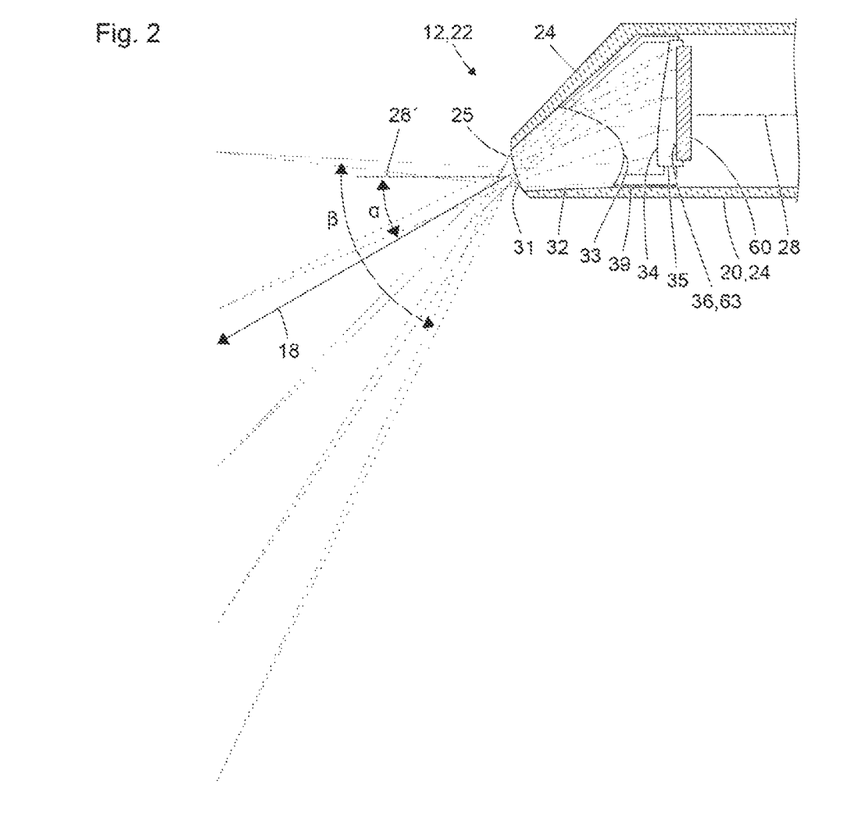
FIG. 2 shows a schematic illustration of a distal end of an endoscope.

FIG. 2 shows a schematic illustration of a section through a distal end 12 of an endoscope which, in terms of some features, properties and functions, may be similar to the endoscope presented on the basis of FIG. 1. The sectional plane of FIG. 2 contains a longitudinal axis 28 of the distal end 22 of the shaft 20, said longitudinal axis being presented in FIG. 2 as an axis of symmetry of the outer surface of a barrel component 24 of the shaft 20. Sectional areas of optically non-transparent components are illustrated in hatched fashion in FIG. 2. Sectional areas of optically transparent components are illustrated without hatching in FIG. 2.

The viewing direction 18 of the endoscope 10 includes an angle α (alpha) with the longitudinal axis 28 of the shaft 20 and with a parallel 28' thereof. The visual field or the field of view of the endoscope comprises an angle β (beta).

An opening 25 is provided in the optically non-transparent barrel component 24 at the distal end 22 of the shaft 20. A first optically transparent body 32 seals the opening 25 of the barrel component 24, particularly in fluid-tight or hermetic fashion. A light-entrance surface 31 of the first transparent body 32 forms a light-entrance surface of the endoscope. In the example illustrated in FIG. 2, the light-entrance surface 31 of the first transparent body 32 is arranged flush with the outer surface of the barrel component 24 of the shaft 20. The first transparent body 32 has a light-exit surface 33. In the illustrated example, both the light-entrance surface 31 and the light-exit surface 33 of the first transparent body 32 are curved.

Further, a second optically transparent body 35 with a light-entrance surface 34 and a light-exit surface 36 is arranged at the distal end 22 of the shaft 20 and within the barrel component 24. The second transparent body 35 can be printed directly on the image sensor 60 or be produced directly on the light-entrance surface 63 of the image sensor 60 in any other way and cohesively connected to the latter in the process. Alternatively, the second transparent body 35 may initially be produced separately, following which the light-exit surface 36 thereof is joined to a light-entrance surface 63 of the image sensor 60.

As indicated in FIG. 2, the second transparent body 35 can have a cutout, in which the image sensor 60 has been inserted. An interlock between the cutout and the image sensor 60 may facilitate a precise alignment of the image sensor 60 relative to the second transparent body 35, even in the case of an initially separate production.

A plurality of support struts 39 connect the first transparent body 32 and the second transparent body 35 in mechanically rigid fashion. The ends of the support struts 39 are connected to the edge regions of the first transparent body 32 and of the second transparent body 35. In the illustrated example, the support struts 39 lie outside of the sectional plane illustrated in FIG. 2. Hence, the contours of the support struts 39 are indicated using dashed lines.

In particular, the transparent bodies 32, 35 and the support struts 39 are formed at the same time and from the same optically transparent material. The optically transparent bodies 32, 35 and, optionally, the support struts 39, too, are formed, in particular, by means of a 3D printing method based on two-photon absorption. Alternatively, one of the transparent bodies 32, 35 or both transparent bodies 32, 35 can be produced by casting in a mold, wherein the mold is produced, in particular, by 3D printing, which may be based on two-photon absorption.

Alternatively, the transparent bodies 32, 35 can be formed from different materials. Each of the two transparent bodies 32, 35 may alternatively be formed from a plurality of partial bodies made of different materials in order, for example, to reduce a chromatic aberration.

Further, an image sensor 60 is arranged within the barrel component 24 in the vicinity of the distal end 22 of the shaft 20. A light-entrance surface 63 of the image sensor 60 abuts on the plane light-exit surface 36 of the second transparent body 35 in planar fashion and is connected to the latter, particularly in a cohesive manner. The image sensor 60 has a multiplicity of small light-sensitive regions, which are referred to as picture elements or pixels, for example in a matrix-shaped arrangement. These picture elements or pixels are arranged in a thin layer near the light-entrance surface 63 of the image sensor 60. For simplification purposes, the assumption is made here that the picture elements or pixels are arranged directly at the light-entrance surface 63 of the image sensor 60.

An image produced in the matrix-shaped arrangement of picture elements or pixels is captured by the image sensor 60. The image sensor 60 produces an analog or digital and, in particular, electrical image signal, which represents the captured image.

Light emanating from an object outside of the endoscope can enter into the distal end 12 of the endoscope through the light-entrance surface 31 of the first transparent body 32, emerge from the first transparent body 32 through the light-exit surface 33 of the first transparent body 32, enter into the second transparent body 35 through the light-entrance surface 34 of the latter, emerge from the second transparent body 35 through the light-exit surface 36 of the latter and, at the same time, enter into the image sensor 60 through the light-entrance surface 63 of the latter. The light-entrance surface 31 and the light-exit surface 33 of the first transparent body 32 and the light-entrance surface 34 of the second transparent body 35 are curved in each case. In FIG. 2, the light-exit surface 33 of the first transparent body 32 and the light-entrance surface 34 of the second transparent body 35, in particular, are each indicated as being aspherically (i.e., not spherically) curved.

The first transparent body 32 has a refractive index that differs from the refractive index of the medium (in particular, air or carbon dioxide or any other gas or water or an aqueous solution), in which the distal end 22 of the shaft 20 is situated during the intended use of the endoscope. Therefore, the light-entrance surface 31 of the first transparent body 32 is a light-refracting interface. A medium (e.g., air or nitrogen), the refractive index of which differs from the refractive indices of the materials of the transparent bodies 32, 35, is situated between the transparent bodies 32, 35. Therefore, the light-exit surface 33 of the first transparent body 32 and the light-entrance surface 34 of the second transparent body 35 are light-refracting interfaces.

Should the refractive indices of the materials of the second transparent body 35 and of the image sensor 60 differ, the interface formed by the light-exit surface 36 of the second transparent body 35 and the light-entrance surface 63 of the image sensor 60 is also light-refracting. The light-refracting property of this interface 36, 63 between the second transparent body 35 and the image sensor 60 however only plays a role to the extent that the light-sensitive regions of the image sensor 60, which are referred to as picture elements or pixels and which are used to produce an image signal, are spaced apart from the light-entrance surface 63 of the image sensor 60. As already mentioned, the simplifying assumption is made here that these light-sensitive regions of the image sensor 60 are thin and arranged directly at the light-entrance surface 63 of the image sensor 60.

Each of the light-refracting interfaces 31, 33, 34 is curved. Each of the light-refracting interfaces 31, 33, is curved aspherically, in particular. This is indicated in identifiable fashion in FIG. 2, particularly in the case of the light-exit surface 33 of the first transparent body 32. In particular, each of the light-refracting interfaces 31, 33, 34 is not rotationally symmetric either. This is indicated in identifiable fashion in the illustration of FIG. 2, particularly in the case of the light-refracting interfaces 33, 34. Further, each of the light-refracting interfaces 31, 33, 34 is, in particular, not a section of a rotationally symmetric area either. Each of the light-refracting interfaces 31, 33, 34 is embodied as a free-form surface, in particular, and describable, for example, at least in piecewise fashion by one or more polynomial functions.

At least some of the light-refracting interfaces 31, 33, (all light-refracting interfaces 31, 33, 34 in the example illustrated in FIG. 2) are tilted in relation to one another and/or in relation to the longitudinal axis 28 of the distal end 22 of the shaft 20 and the surface normal of the light-entrance surface 63 of the image sensor 60. In particular, this means that the surface normals of the light-refracting interfaces 31, 33, 34, at the surface center points or at their vertices or at their points with maximum curvature, or the surface normals of the light-refracting interfaces, in each case averaged over the interfaces, are not parallel to one another and/or not parallel to the longitudinal axis 28 of the shaft 20 or to the surface normal of the light-entrance surface 63 of the image sensor 60.

Light emanating from objects outside of the distal end 22 of the shaft 20 can enter into the shaft 20 through the light-entrance surface 31 and can be refracted by the light-entrance surface 31 and the further light-refracting interfaces 33, 34. The first transparent body 32 and the second transparent body 35 form an optical imaging device, which, in the picture elements or pixels of the image sensor 60 at the light-entrance surface 63 thereof, produces a sharp image of objects within an intended object area. This is indicated by dashed lines in FIG. 2.

In the illustrated example, the curved, at least partly neither spherically nor otherwise rotationally symmetrically curved light-refracting interfaces 31, 33, 34, which are tilted in relation to one another, cause the viewing direction 18 to be not parallel to the longitudinal axis 28 of the shaft 20 at the distal end 22 thereof and not parallel to the surface normal of the light-entrance surface 63 of the image sensor 60, the predetermined object area, which is imaged in focus, to be plane or substantially plane and the predetermined object area, which is imaged in focus, to be orthogonal or substantially orthogonal to the longitudinal axis 28 of the shaft 20 at the distal end 22 thereof. Further, the at least partly aspherical and not rotationally symmetric configuration and arrangement of the light-refracting interfaces 31, 33, 34, which are tilted in relation to one another, may cause a distortion of the produced image, i.e., a variation in the imaging scale within the image and depending on the direction.

Figure 3:
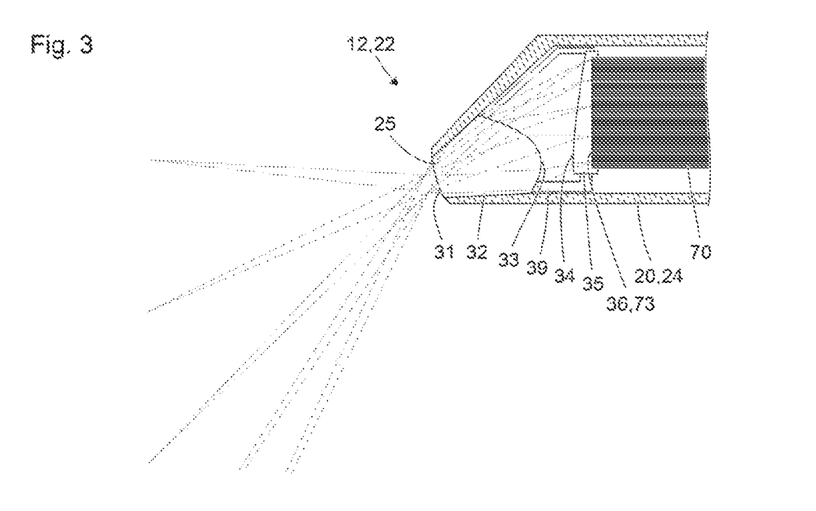
FIG. 3 shows a schematic illustration of a distal end of a further endoscope.

FIG. 3 shows a schematic illustration of a section through the distal end 12 of a further endoscope, which is similar to the endoscopes illustrated on the basis of FIGS. 1 and 2 in terms of some features, properties and functions. The type of illustration, in particular the position and orientation of the sectional plane, corresponds to that of FIG. 2. In particular, features, properties and functions in which the endoscope whose distal end 12 is illustrated in FIG. 3 differs from the endoscopes illustrated on the basis of FIGS. 1 and 2 are described below.

The endoscope whose distal end is illustrated in FIG. 3 differs from the endoscope presented on the basis of FIG. 2 in that, in particular, no image sensor is provided at the distal end 22 of the shaft 20. Instead, the endoscope has an image transfer device 70, which is illustrated in exemplary fashion in FIG. 3 as a coherent bundle of optical fibers.

A light-entrance surface 73 of the image transfer device 70 abuts against the light-exit surface 36 of the second transparent body 35 in planar fashion and can be joined to the latter in planar fashion, for example by adhesive bonding or welding. Alternatively, the second transparent body 35 can be produced directly at the distal end of the image transfer device 70, for example by 3D printing, and can be connected in cohesive fashion to the light-entrance surface 73 of the image transfer device 70 in the process.

Figure 4:
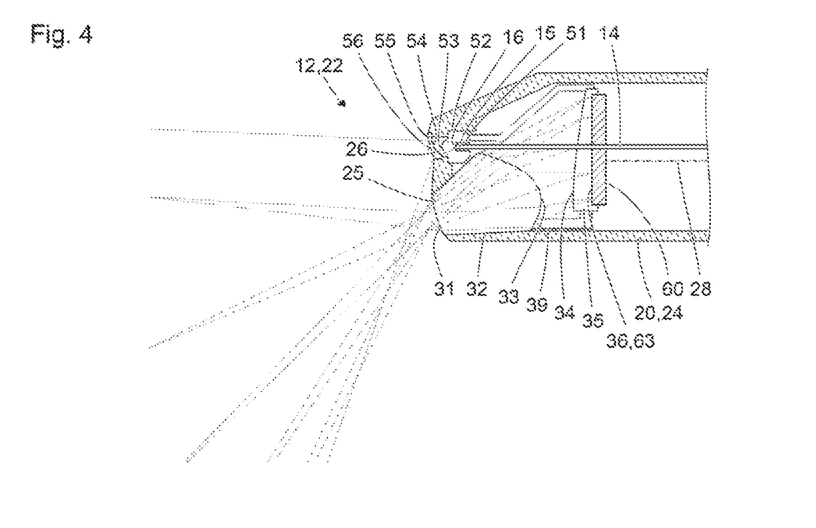
FIG. 4 shows a schematic illustration of a distal end of a further endoscope.

FIG. 4 shows a schematic illustration of a section through a distal end 12 of the further endoscope, which is similar to the endoscopes illustrated on the basis of FIGS. 1 to 3, in particular to the endoscope illustrated on the basis of FIG. 2, in terms of some features, properties and functions. The type of illustration, in particular the position and orientation of the sectional plane, corresponds to that of FIGS. 2 and 3. In particular, features, properties and functions in terms of which the endoscope whose distal end 12 is illustrated in FIG. 4 differs from the endoscopes illustrated on the basis of FIGS. 1 to 3 are described below.

The endoscope whose distal end 12 is illustrated in FIG. 4 comprises a light guide 14, which extends in the shaft 20 of the endoscope from its proximal end to its distal end 12. The distal end 15 of the light guide 14 is arranged in a bore 51 in a first transparent body 52 of a light-steering device. In addition to the first transparent body 52, the light-steering device comprises a second transparent body 55, which seals a second opening 26 in the barrel component 24 in fluid-tight or hermetic fashion.

The first transparent body 52 of the light-guiding device has a curved light-exit surface 53, which is arranged on a side, facing away from the cutout 51, of the first transparent body 52 of the light-steering device. The cutout 51 defines, in interlocking fashion, the position and orientation of the distal end 15 of the light guide 14 and hence also of a light-exit surface 16 of the light guide 14 relative to the light-exit surface 53 of the first transparent body 52 of the light-steering device. The distal end 15 of the light guide 14 is cohesively fastened in the cutout 51 of the first transparent body 52 of the light-steering device, for example by adhesive bonding or welding.

The second transparent body 55 of the light-steering device comprises a light-entrance surface 54 facing the light-exit surface 53 of the first transparent body 52 and a light-exit surface 56 at the side facing away from the light-entrance surface 54. The light-exit surface 56 of the second transparent body 55 is part of the outer surface of the distal end 22 of the shaft 20 of the endoscope. In the illustrated example, the light-exit surface 56 of the second transparent body 55 of the light-steering device is arranged flush with the surrounding regions of the outer surface of the barrel component 24.

The first transparent body 52 and the second transparent body 55 of the light-steering device may comprise the same or different materials with different refractive indices. The refractive indices of the materials of the transparent bodies 52, 55 of the light-steering device differ from the refractive index of the gas (e.g., air or nitrogen) in the interstice between the transparent bodies 52, 55 in the second opening 26 in the barrel component 24. Hence, the light-exit surface 53 of the first transparent body and the light-entrance surface 54 of the second transparent body 55 of the light-steering device are light-refracting interfaces. The second transparent body 55 of the light-steering device comprises a refractive index that differs from the refractive index of the medium (in particular, air or carbon dioxide or any other gas or water or an aqueous solution), in which the distal end 22 of the shaft 20 is situated in the case of the intended use of the endoscope. Therefore, the light-exit surface 56 of the second transparent body 55 of the light-steering device, too, is a light-refracting interface.

In the illustrated example, the light-entrance surface of the second transparent body 55 of the light-steering device is curved; the light-exit surface 56 of the second transparent body 55 is plane. In particular, at least one of the light-refracting interfaces 53, 54, 56 is aspherical, not rotationally symmetric or not a section of a rotationally symmetric surface.

Further, within the meaning described above for the light-refracting interfaces 31, 33, 34 of the optical imaging device 32, 35, the light-refracting interfaces 53, 54, 56 are tilted in relation to one another in the illustrated example.

By means of their curved light-refracting interfaces 53, 54, 56, which are tilted in relation to one another, the transparent bodies 52, 55 of the light-steering device control the distribution of the illumination light, said illumination light being transferred by the light guide 14 to the distal end 12 of the endoscope and passing through the transparent bodies 52, 55 of the light-steering device and emerging from the distal end 22 of the shaft 20. In particular, the distribution of the illumination light is matched to the visual field or the field of view of the endoscope. The light flux emanating from the distal end 15 of the light guide 14 and the boundaries of the illuminated region are indicated by thin dotted lines in FIG. 4.

The light guide 14 can transfer illumination light, which is produced by a light source in the proximal end of the endoscope or transferred to the proximal end of the endoscope from an external light source by means of a light-guiding cable, to the distal end 12 of the endoscope. Alternatively, the light guide 14 can transfer illumination light, which is produced by a light source in the shaft 20 in the vicinity of the distal end thereof, to the light-steering device 52, 55. As an alternative thereto and deviating from the illustration in FIG. 4, a light source may be provided in place of the light guide 14, said light source being arranged directly at the light-steering device 52, 55, for example in the cutout 51 or at a light-entrance surface of the first transparent body 52 of the light-steering device.

In the example illustrated in FIG. 4, the endoscope comprises an image sensor 60 within the barrel component 24, near the distal end 22 of the shaft 20 and similar to what is the case in the example illustrated on the basis of FIG. 2. Alternatively, an image transfer device, for example a coherent bundle of optical fibers as illustrated on the basis of FIG. 3, can be provided instead of the image sensor 60.

Figure 5:
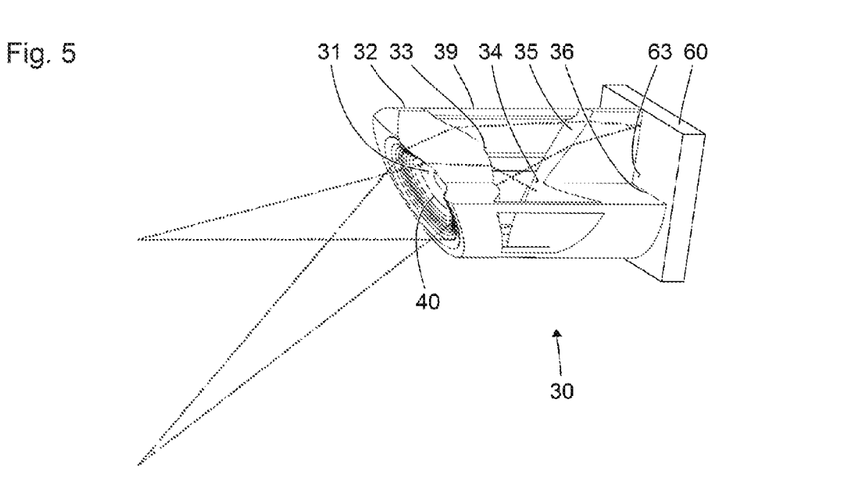
FIG. 5 shows a schematic axonometric illustration of an imaging device.

FIG. 5 shows a schematic axonometric illustration of an optical imaging device 30 and of an image sensor 60, which are similar to the imaging devices of the endoscopes illustrated on the basis of FIGS. 2 to 4 in terms of some features, properties and functions. The imaging device 30 is illustrated partly cut open such that contours of sectional planes along two orthogonal semi-planes are visible. The image sensor 60 is illustrated in simple axonometric fashion without a section and, simplified, as a cuboid.

Like in the examples illustrated on the basis of FIGS. 2 to 4, curved light-entrance surfaces and light-exit surfaces 31, 33, 34, which are tilted in relation to one another, of two transparent bodies 32, 35 form light-refracting interfaces with an imaging effect. A light-exit surface 36 of the second transparent body 35 is joined to a light-entrance surface 63 of the image sensor 60. The curvature of the light-refracting interfaces 31, 33, 34 and their arrangement tilted in relation to one another and in relation to the light-entrance surface 63 of the image sensor 60 create a viewing direction that is not orthogonal to the light-entrance surface 63 of the image sensor 60.

A diffractive optical element 40 made of a plurality of ring-shaped steps (but by no means necessarily circular-ring-shaped steps) is provided at the light-entrance surface 31 of the first transparent body 32. The diffractive optical element 40 has an anomalous dispersion and can correct or reduce the chromatic aberration of the optical imaging device 30 in this way.

Deviating from the illustration in FIG. 5, a diffractive optical element can be provided at the light-exit surface 33 of the first transparent body 32 or at the light-entrance surface 34 of the second transparent body 35 of the optical imaging device 30 as an alternative or in addition to the diffractive element 40 at the light-entrance surface 31 of the first transparent body 32.

The first body 32 and the second body 35 of the optical imaging device 30 are mechanically rigidly interconnected by a plurality of parallel support struts 39, which form a cage-like shape with the transparent bodies 32, 35. The transparent bodies 32, 35 and the support struts 39 can be formed from the same material or, in particular, be produced during the same production step—for example, by 3D printing.

Figure 6:
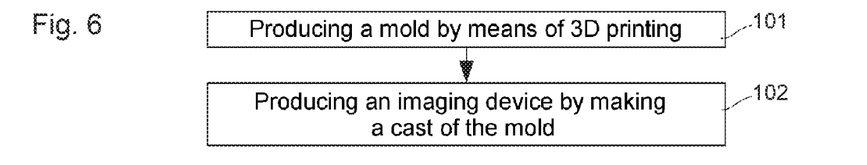
FIG. 6 shows a schematic flow chart of a method for producing an imaging device.

FIG. 6 shows a schematic flowchart of a method for producing an imaging device for an endoscope. In particular, the method is suitable for producing an imaging device with the properties illustrated on the basis of FIGS. 2 to 5 and/or for an endoscope as illustrated on the basis of FIGS. 1 to 4. However, the method is also suitable for producing an imaging device which has features, characteristics and functions that deviate from what is illustrated on the basis of FIGS. 1 to 5. Below, reference signs of FIGS. 1 to 5 are used in exemplary fashion in order to simplify the understanding.

A mold is produced in a first step 101 by means of 3D printing. An imaging device is produced in a second step 102 by making a cast of the mold. The mold can be embodied as an expendable mold, which needs to be destroyed after casting in order to completely expose the imaging device as a cast part. Alternatively, the mold can be reusable.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS

10 Endoscope
11 Proximal end of the endoscope 10
12 Distal end of the endoscope 10
14 Light guide for transferring illumination light
15 Distal end of the light guide 14
16 Light-exit surface of the light guide 14
18 Viewing direction of the endoscope 10
20 Shaft of the endoscope 10
21 Proximal end of the shaft 20
22 Distal end of the shaft 20
24 Barrel component of the shaft 20
25 First opening in the barrel component 24, for receiving the first transparent body 32 of the optical imaging device 30
26 Second opening in the barrel component 24, for receiving the first transparent body 52 of the light-steering device 50
28 Longitudinal axis of the shaft 20 or of the distal end 23 of the shaft 20
28' Parallel of the longitudinal axis 28
30 Optical imaging device at the distal end 23 of the shaft 20
31 Light-entrance surface of the first transparent body 32, of the optical imaging device 30 and of the endoscope 10
32 First transparent body of the optical imaging device 30
33 Light-exit surface of the first transparent body 32 of the optical imaging device 30
34 Light-entrance surface of the second transparent body 35 of the optical imaging device 30
35 Second transparent body of the optical imaging device 30
36 Light-exit surface of the second transparent body of the optical imaging device 30
39 Support struts for rigidly mechanically interconnecting the first transparent body 32 and the second transparent body 35 of the optical imaging device 30
40 Step-shaped structure at the light-entrance surface 31 of the first transparent body 32 as a diffractive optical element
51 Cutout in the first transparent body 52 of the light-steering device for receiving the distal end of the light guide 15
52 First transparent body of the light-steering device
53 Light-exit surface of the first transparent body 52 of the light-steering device
54 Light-entrance surface of the second transparent body 55 of the light-steering device
55 Second transparent body of the light-steering device
56 Light-exit surface of the second transparent body 55 of the light-steering device
60 Image sensor
63 Light-entrance surface of the image sensor 60
70 Image transfer device
73 Light-entrance surface of the image transfer device 70
101 First step (producing a mold by means of 3D printing)
102 Second step (producing an imaging device by casting into the mold)

We claim:

1. A medical endoscope, comprising:
   a shaft comprising a distal end;
   an optical imaging device at the distal end of the shaft for producing a real image of an object observed by means of the endo scope;
   at least one of an image transfer device for transmitting the real image and an image sensor for capturing the real image;
   wherein the imaging device has curved light-refracting interfaces, which are tilted in relation to one another;
   wherein a viewing direction of the endo scope is not parallel to a longitudinal axis of the distal end of the shaft of the endo scope; and
   wherein no reflecting surface is provided upstream of the real image in relation to a light flux.

2. The medical endoscope according to claim 1, wherein one of the curved light-refracting interfaces of the imaging device is not rotationally symmetric.

3. The medical endoscope according to claim 1, wherein one of the curved light-refracting interfaces of the imaging device is not a section of a rotationally symmetric curved surface.

4. The medical endoscope according to claim 1, wherein:
   the imaging device is produced by means of 3D printing,
   the imaging device is printed directly on a distal light-entrance surface of the image transfer device for transmitting the real image or on a light-entrance surface of the image sensor for capturing the real image.

5. The medical endoscope according to claim 1, wherein the imaging device is produced from a plurality of different materials by means of 3D printing.

6. The medical endo scope according to claim 1, further comprising:
   a light-steering device at the distal end of the endo scope for steering illumination light emanating from a distal light-exit surface of a light guide or from a light-exit surface of a light source,
   wherein the light-steering device has a light-refracting interface, is tilted in relation to a longitudinal axis of a distal end of the light guide or in relation to a surface normal of the light-exit surface of the light source.

7. The medical endo scope according to claim 6, wherein at least one of:
   being mechanically rigidly connected to one another, and
   having the same optically transparent material, and
   having a monolithic embodiment, and
   being produced at the same time,
   applies to the imaging device and the light-steering device.

8. The medical endoscope according to claim 6, further comprising:
   a support frame, which rigidly connects the imaging device and the light-steering device to one another.

9. The medical endo scope according to claim 6, wherein:
   the light-steering device has a cutout for receiving the distal end of the light guide, the cutout defines a position and orientation of the distal end of the light guide.

10. The medical endoscope according to claim 1, wherein:
    the imaging device is produced by means of 3D printing based on multi-photon absorption or multi-photon polymerization.

11. The medical endoscope according to claim 1, wherein:
    the imaging device comprises an interface embodied as a diffractive optical element or any other diffractive optical element.

12. The medical endoscope according to claim 1, wherein:
    the imaging device comprises a plurality of optically transparent bodies with the light-refracting interfaces, said bodies being penetrated by light that emanates from an observed object and contributes to the production of the real image,
    a supporting device mechanically rigidly connects the bodies,
    the supporting device and the transparent bodies are at least one of formed by the same material and produced at the same time.

13. The medical endoscope according to claim 1, wherein:
    the image device are not rotationally symmetric.

* * * * *